(12) United States Patent
Hashimoto et al.

(10) Patent No.: US 9,381,121 B2
(45) Date of Patent: Jul. 5, 2016

(54) DISPOSABLE WEARING ARTICLE

(71) Applicant: UNICHARM CORPORATION, Shikokuchuo-shi, Ehime (JP)

(72) Inventors: Tatsuya Hashimoto, Kanonji (JP); Tetsuo Okubo, Kanonji (JP); Toshifumi Otsubo, Kanonji (JP); Hiroyuki Tanji, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 34 days.

(21) Appl. No.: 14/388,674

(22) PCT Filed: Mar. 27, 2013

(86) PCT No.: PCT/JP2013/058918
§ 371 (c)(1),
(2) Date: Sep. 26, 2014

(87) PCT Pub. No.: WO2013/146842
PCT Pub. Date: Oct. 3, 2013

(65) Prior Publication Data
US 2015/0051569 A1 Feb. 19, 2015

(30) Foreign Application Priority Data

Mar. 29, 2012 (JP) .................................. 2012-077849
Mar. 8, 2013 (JP) .................................. 2013-047401

(51) Int. Cl.
*A61F 13/15* (2006.01)
*A61F 13/49* (2006.01)
(Continued)

(52) U.S. Cl.
CPC ..... *A61F 13/49012* (2013.01); *A61F 13/15593* (2013.01); *A61F 13/15699* (2013.01);
(Continued)

(58) Field of Classification Search
CPC .................... A61F 13/49007; A61F 13/49009; A61F 13/49011; A61F 13/19012; A61F 13/49017; A61F 13/19019; A61F 13/19058; A61F 13/4906; A61F 13/49061; A61F 13/49406; A61F 13/49413; A61F 13/4942; A61F 13/49466; A61F 13/496
See application file for complete search history.

(56) References Cited

U.S. PATENT DOCUMENTS

| 2010/0324519 A1* | 12/2010 | Shimada et al. ........... 604/385.3 |
| 2011/0071488 A1 | 3/2011 | Kuwano et al. |
| 2011/0106039 A1* | 5/2011 | Saito et al. ................. 604/385.3 |

FOREIGN PATENT DOCUMENTS

| EP | 2295013 A1 | 3/2011 |
| EP | 2520259 A1 | 11/2012 |

(Continued)

OTHER PUBLICATIONS

International Search Report mailed May 7, 2013 in International Application No. PCT/JP2013/058918 filed Mar. 27, 2013.

(Continued)

*Primary Examiner* — Bradley Philips
(74) *Attorney, Agent, or Firm* — Hauptman Ham, LLP

(57) ABSTRACT

A disposable wearing article includes, in an inner end portion of a front waist region, a pair of first side elastic zones spaced apart from each other in a transverse direction and a first middle inelastic zone lying between the first side elastic zones. The article further includes, in an inner end portion of a rear waist region, a pair of second side elastic zones spaced apart from each other in the transverse direction and a second middle inelastic zone lying between the second side elastic zones. A crotch panel includes a pair of leg elastics intersecting with the first and second side elastic zones. A dimension in the transverse direction of the second middle inelastic zone is larger than that of the first middle inelastic zone. A dimension in the transverse direction of the respective first intersection zones is larger than that of the respective second intersection zones.

9 Claims, 13 Drawing Sheets

(51) Int. Cl.
  *A61F 13/496* (2006.01)
  *A61F 13/494* (2006.01)

(52) U.S. Cl.
  CPC ......... *A61F13/15756* (2013.01); *A61F 13/496* (2013.01); *A61F 13/49011* (2013.01); *A61F 13/49017* (2013.01); *A61F 13/49061* (2013.01); *A61F 13/49406* (2013.01); *A61F 13/49413* (2013.01); *A61F 13/49466* (2013.01)

(56) References Cited

FOREIGN PATENT DOCUMENTS

| | | |
|---|---|---|
| JP | 2004-49765 A | 2/2004 |
| JP | 2009-119079 A | 6/2009 |
| JP | 2009-240640 A | 10/2009 |
| JP | 2011-98052 A | 5/2011 |
| JP | 2011-177285 A | 9/2011 |
| WO | 2011/081027 A1 | 7/2011 |

OTHER PUBLICATIONS

Written Opinion of the International Searching Authority mailed May 7, 2013 in corresponding International Application No. PCT/JP2013/058918 filed Mar. 27, 2013.

Extended European Search Report dated Oct. 6, 2015, corresponding to European Application No. 13768227.4.

* cited by examiner (a)

front side (b)

rear side

DISPOSABLE WEARING ARTICLE

RELATED APPLICATIONS

The present application is a National Phase of International Application Number PCT/JP2013/058918, filed Mar. 27, 2013, which claims priority to Japanese Application Number 2012-077849, filed Mar. 29, 2012 and Japanese Application Number 2013-047401, filed Mar. 8, 2013.

TECHNICAL FIELD

The present invention relates to disposable wearing articles and, more specifically, to disposable wearing articles such as pant-type disposable diapers, disposable toilet-training pants and disposable incontinent pants each provided with waist elastics.

BACKGROUND

Conventionally, disposable wearing articles provided with waist elastics are known. For example, JP 2011-98052 A (PLT 1) discloses a disposable wearing article including an absorbent structure extending across a crotch region into front and rear waist regions and provided along lateral edges thereof with a plurality of thread, strand or string elastics and front and rear waist panels provided with a plurality of thread, strand or string waist elastics extending in a transverse direction in front and rear waist regions, respectively.

CITATION LIST

Patent Literature

{PLT 1}: JP 2011-98052 A

SUMMARY

Technical Problem

In this disposable wearing article, according to the disclosure of PLT 1, elastic cuffs including leg elastics are attached to the lateral edges of the absorbent structure in the front waist region in a state of being laid inwardly as viewed in the transverse direction and, in the rear waist region, these elastic cuffs are attached to the rear waist panel in a state of being laid outward as viewed in the transverse direction. With such an arrangement, body exudate are unlikely to leak out of the front waist region and, in the rear waist region, a distance between the paired elastic cuffs may be maintained sufficiently large to prevent the width dimension of the absorbent structure from being unacceptably constricted to expose a wide range of the wearers buttocks.

However, the waist elastics and the leg elastics constituting the elastic cuffs overlap with each other in the rear waist region, so elongation and contraction of the waist elastics may interfere with elongation of the leg elastics in the leg-circumferential direction. Thus, the absorbent structure may be partially caught between the thighs and, as a result, the buttocks may be partially exposed, disfiguring the wearing appearance.

An object of the present invention is to provide a disposable wearing article adapted to ensure a desired fit in the front waist region and to make the leg elastics free from interference from elongation and contraction of the waist elastics without disfiguring the article as viewed from the back.

Solution to Problem

According to the present invention, there is provided a disposable wearing article having a longitudinal direction and a transverse direction being orthogonal to the longitudinal direction and including a skin-facing surface, a non-skin-facing surface, a front waist region, a rear waist region, a crotch region extending between the front and rear waist regions, an annular elastic waist panel defining the front and rear waist regions, a crotch panel defining the crotch region and an absorbent structure joined to the elastic waist panel.

The disposable wearing article according to the present invention further includes the following features:

the front waist region includes outer and inner end edges spaced apart from and opposite to each other in the longitudinal direction, a pair of first side elastic zones extending in the transverse direction and spaced apart from and opposite to each other in the transverse direction and a first middle inelastic zone lying between the first side elastic zones;

the rear waist region includes outer and inner end edges spaced apart from and opposite to each other in the longitudinal direction, a pair of second side elastic zones extending in the transverse direction and spaced apart from and opposite to each other in the transverse direction and a second middle inelastic zone lying between the first side elastic zones;

the crotch panel includes a front end portion secured to the front waist region, a rear end portion secured to the rear waist region and a pair of leg elastics extending in the longitudinal direction and intersecting with the first and second side elastic zones;

a dimension in the transverse direction of the second middle inelastic zone is larger than a dimension in the transverse direction of the first middle inelastic zone; and a dimension in the transverse direction of a first intersection zone in which the first side elastic zone and the leg elastics intersect with each other is larger than a dimension in the transverse direction of a second intersection zone in which the second side elastic zone and leg elastics intersect with each other.

Advantageous Effects of Invention

In the disposable wearing article according to the present invention, the dimension in the transverse direction of the second middle inelastic zone defined between the second side elastic zones in the rear waist region is larger than the dimension in the transverse direction of the first middle inelastic zone defined between the first side elastic zones in the front waist region and, in consequence, the contractile force of the second side elastic zones should not interfere with the absorptive property of the absorbent structure in the rear waist region. In this way, the wearers buttocks may be reliably covered and it is ensured that the front waist region can conform to the movement of the wearer's thighs under the effect of the tensile strength of the first side elastic zones. The length dimension in the transverse direction of the respective second intersection zones in which the second side elastic zones intersect with the leg elastics in the rear waist region is smaller than the length dimension in the transverse direction of the respective first intersection zones in which the first side elastic zones intersect with the leg elastics. With this arrangement, the leg elastics should not be pulled inwardly under the contraction of the second side elastic zones to constrict the width of the crotch region and the wearer's buttocks should not be exposed externally to disfigure the wearing article.

DESCRIPTION OF EMBODIMENTS

First Embodiment

Figure 1:
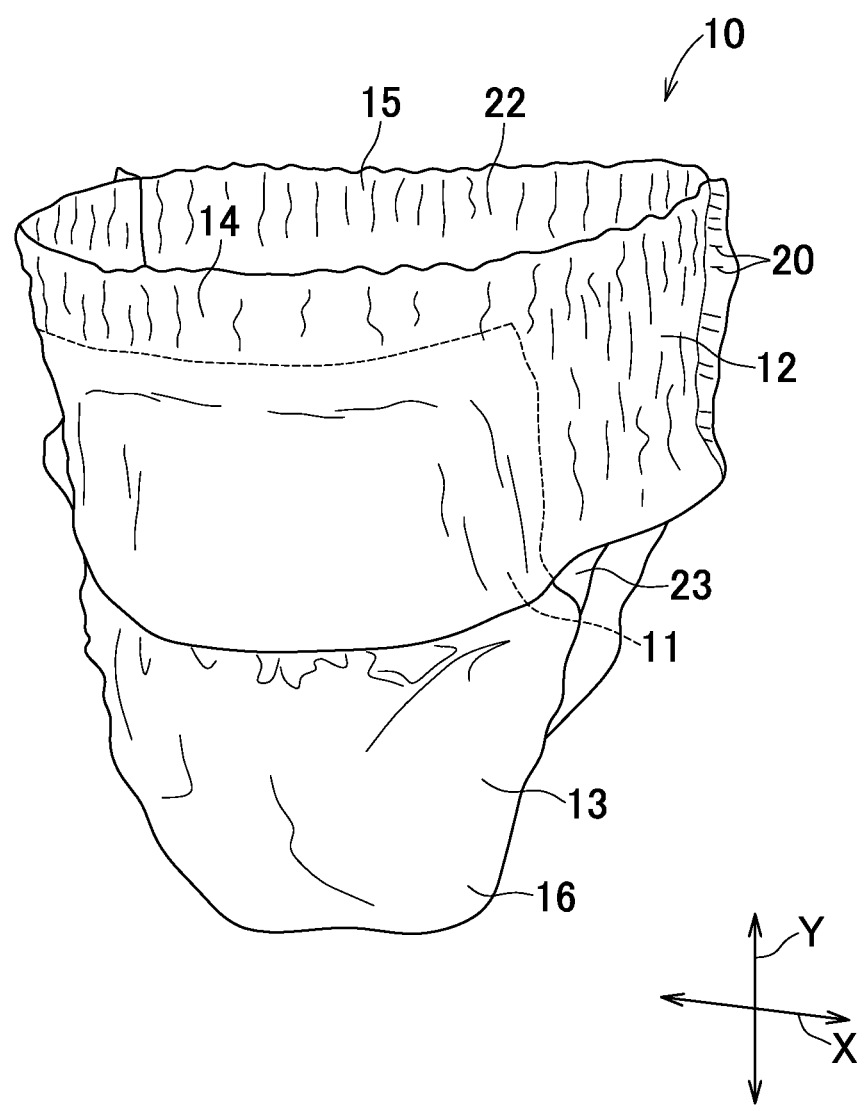
FIG. 1 is a perspective view exemplifying a disposable diaper according to a first embodiment as an example of the disposable wearing article according to the present invention.
Figure 2:
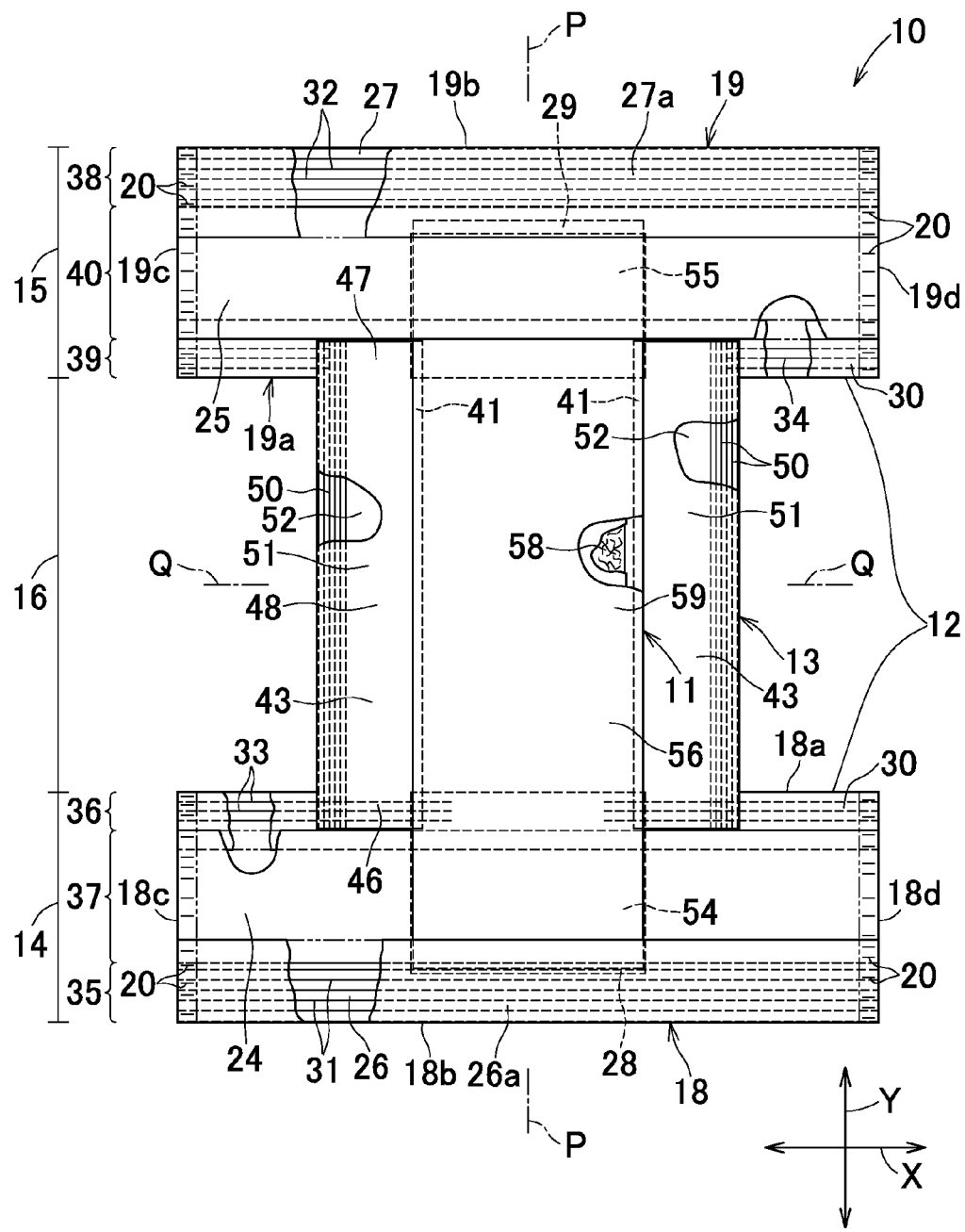
FIG. 2 is a partially cutaway developed plan view illustrating the diaper flatly extended in a longitudinal direction and a transverse direction to a maximum elongation points of respective elastics, wherein gathers/creases/wrinkles due to the contractile force of the elastics are visually disappeared.
Figure 3:
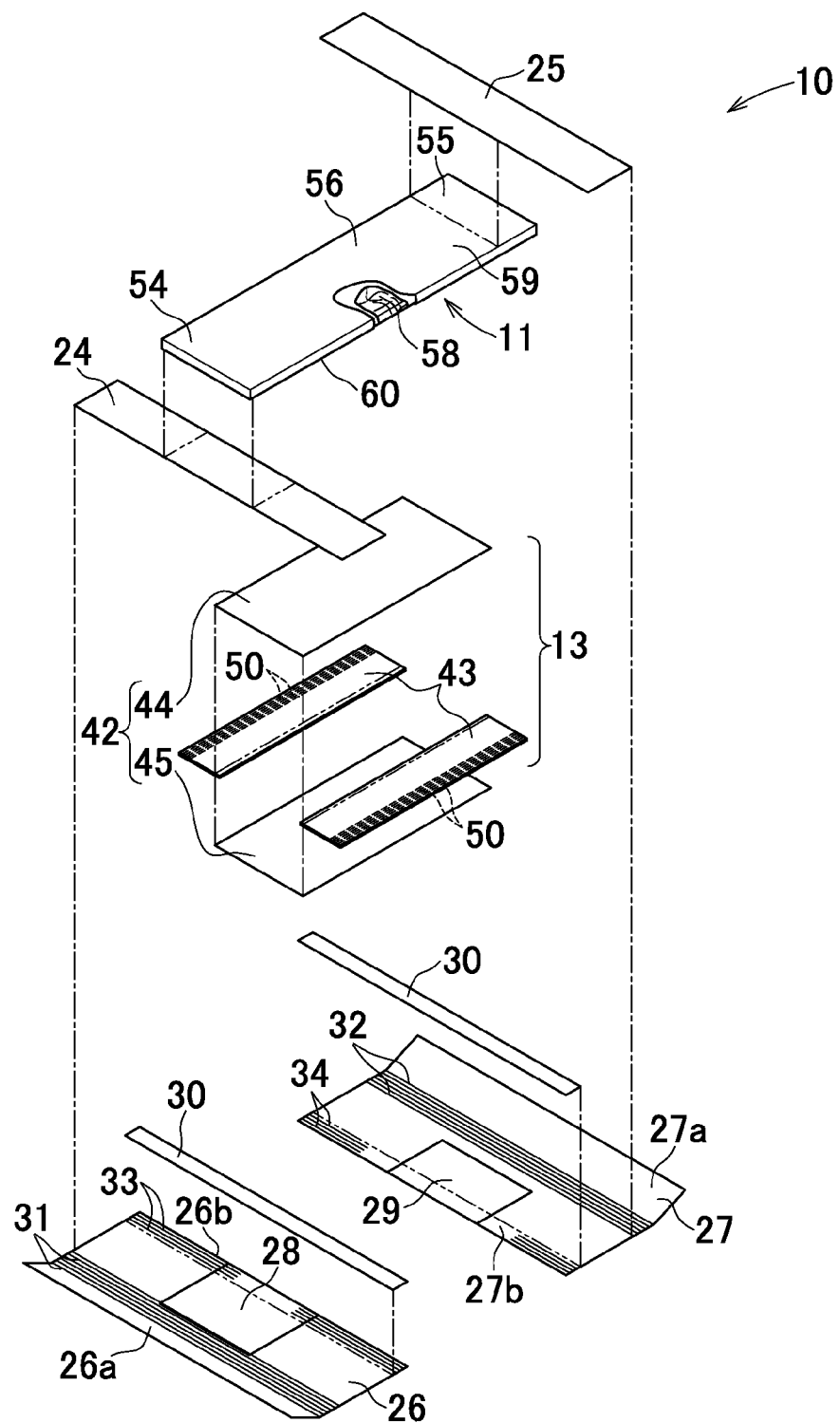
FIG. 3 is an exploded perspective view of the diaper.

Referring to FIGS. 1 through 3, a disposable diaper 10 has a longitudinal axis P-P, a transverse axis Q-Q, a longitudinal direction Y, a transverse direction X, and includes a skin-facing surface, a non-skin-facing surface opposite to the skin-facing surface, an annular elastic waist panel 12 circumferentially extending about a wearer's waist, an absorbent structure 11 joined to the skin-facing surface of the elastic waist panel, and an elastic crotch panel 13 attached to the skin-facing surface of the elastic waist panel 12. The diaper 10 further includes a front waist region 14, a rear waist region 15 and a crotch region 16 extending between the front and rear waist regions 14, 15 and is symmetrically about the longitudinal axis P-P.

The elastic waist panel 12 functions as an elastic belt adapted to stably put the absorbent structure 11 to a crotch region of the wearer and includes a front waist panel 18 defining the front waist region 14 and a rear waist panel 19 defining the rear waist region 15. The front waist panel 18 has a transversely longer rectangular configuration contoured by an inner end edge 18a, an outer end 18b and opposite lateral edges 18c, 18d extending between the inner and outer end edges 18a, 18b, respectively. The rear waist panel 19 also has a transversely longer rectangular configuration contoured by an inner end edge 19a, an outer end 19b and opposite lateral edges 19c, 19d extending between the inner and outer end edges 19a, 19b. The opposite lateral edges 18c, 18d of the front waist panel 18 are put flat with and joined to the associated lateral edges 19c, 19d of the rear waist panel 19 along a pair of series of seams 20 arranged continually in the longitudinal direction with well known heat sealing techniques such as heat-embossing/debossing or ultrasonic sealing techniques and whereby a waist-opening 22 and a pair of leg-openings 23 are defined. In this manner, according to the present invention, the front and rear waist regions 14, 15 are joined to each other along respective lateral edges by means of the seams 20 and the inner end edges 18a, 19a correspond to the lower end edges of the respective joint regions defined by the seams 20.

The front and rear waist panels 18, 19 respectively have inner waist sheets 24, 25 lying on the skin-facing surface and outer waist sheets 26, 27 lying on the non-skin-facing surface. The outer waist sheets 26, 27 respectively have width dimensions in the longitudinal direction Y larger than those of the inner waist sheets 24, 25 and extend outwardly in the longitudinal direction Y beyond inner and outer ends of the respective inner waist sheets 24, 25.

As materials of the outer waist sheets 26, 27, an SMS (spun bonded/melt blown/spun bonded) fibrous nonwoven fabric, a spun bonded fibrous nonwoven fabric, an air-through fibrous nonwoven fabric, a plastic sheet or laminate sheet of the above-mentioned fibrous nonwoven fabrics and the plastic sheet, each having a mass per unit area in a range of about 15 to 30 g/m$^2$ may be used. The inner waist sheets 24, 25 and the outer waist sheets 26, 27 may be respectively bonded to each other with a hot melt adhesive applied to an inner surface of at least one in the respective pair of the inner waist sheet and the outer waist sheet or by the other heat-sealing technique.

As materials of the inner waist sheets 24, 25, an elastic fibrous nonwoven fabric may be used and, for example, an elastic fibrous nonwoven fabric of well known art such as a spun bonded fibrous nonwoven fabric, a melt blown fibrous nonwoven fabric, a heat-rolled fibrous nonwoven fabric, an SMS fibrous nonwoven fabric, an air-laid fibrous nonwoven fabric or an air-through fibrous nonwoven fabric may be used alone or in combination to form these inner waist sheets 24, 25. The elastic nonwoven fabric may be formed of, for example, a polyethylene- or polyurethane-based elastomer resin, or a thermoplastic resin of polyethylene, polypropylene, polyester or acryl. While it is also possible to use an inelastic fibrous nonwoven fabric as a material of the inner waist sheets 24, 25, the inner waist sheet 25 in the rear waist region 14 is adapted to come in direct contact with the wearers skin as will be described later in detail and, for this reason, at least the inner waist sheet 25 is preferably formed of the elastic fibrous nonwoven fabric to improve a flexibility and comfortable texture.

Referring to FIGS. 2 and 3, in middle zones in the transverse direction X of the front and rear waist regions 14, 15, two pieces of graphic display film 28, 29 made of a plastic material and printed the respective non-skin-facing surfaces thereof with visually recognizable graphics (not shown) are interposed between the inner waist sheets 24, 25 and the outer waist sheets 26, 27, respectively. Extension portions of the outer waist sheets 26, 27 extending in the longitudinal direction Y beyond the outer ends of the inner waist sheets 24, 25 are folded inwardly to form folded portions 26a, 27a and first and second waist outer end elastics 31, 32 of threads, strands or strings are contractibly attached under tension in the respective folded portions 26a, 27a with a hot melt adhesive.

Extension portions 26b, 27b extending in the longitudinal direction Y beyond the inner end edges of the inner waist sheets 24, 25 are respectively provided with transversely longer reinforcing sheets 30 formed of fibrous nonwoven fabric and overlapping with the associated extension portions 26b, 27b. Between the reinforcing sheets 30 and the associated extension portions 26b, 27b, first and second inner elastics 33, 34 of threads, strands or strings are contractibly attached under tension with a hot melt adhesive.

The front waist region 14 has an outer end portion 35 provided with the first waist outer end elastics 31, an inner end portion 36 provided with the first waist inner end elastics 33 and an intermediate portion 37 extending between the outer and inner end portions 35, 36. The rear waist region 15 has an outer end portion 38 provided with the first waist outer end elastics 32, an inner end portion 39 provided with the second waist inner end elastics 34 and an intermediate portion 40 extending between the outer and inner end portions 38, 39. The intermediate portions 37, 40 provided with none of the respective elastics are provided with the elastic inner waist sheets 24, 25. In consequence, with the diaper 10 put on the wearer's body, the outer end portions 35, 38 as well as the inner end portions 36, 39 of the front and rear waist regions 14, 15 stably fit the wearer's body and the intermediate portions 37, 40 also fit the wearer's body under the contractile force of the inner waist sheets 24, 25. Thus, the diaper 10 should not be noticeably displaced on the wearer's body, and leakage of bodily fluids from the diaper 10 may be prevented.

The crotch panel 13 has a base sheet 42 lying in a midsection in the transverse direction X and a pair of leg elastic sheets 43 attached to the skin-facing side of the lateral portions of the base sheet 42 by joint regions 41. The base sheet 42 is composed of an inner crotch sheet 44 lying on the side of the skin-facing surface and an outer crotch sheet 45 lying on the side of the non-skin-facing surface. As materials of these inner and outer sheets 44, 45, well known various types of fibrous nonwoven fabrics or plastic films may be used, but the inner crotch sheet 44 is preferably formed of a breathable leakage-barrier plastic film considering that this inner crotch sheet 44 is located so as to face the absorbent structure 11 and the outer crotch sheet 45 is preferably formed of a fibrous nonwoven fabric having a texture more comfortable than that of a plastic film considering that this outer crotch sheet 45 constitute part of the outer surface of the diaper 10.

The crotch panel 13 has front and rear end portions 46, 47 and an intermediate portion 48 extending between the front and rear end portions 46, 47. The front and rear end portions 46, 47 are secured to the skin-facing surface in vicinities of the inner end edges 18a, 19b of the front and rear waist panels 18, 19 in joining zones formed on the non-skin-facing surface of these panels 18, 19 by a hot melt adhesive applied to these zones.

The respective leg elastic sheets 43 include a plurality of leg elastics 50 of threads, strands or strings and leg sheets 51 adapted to interpose the leg elastics 50. Each of the leg sheets 51 is formed of a single fibrous nonwoven fabric or plastic sheet doubled up to sandwich the leg elastics 50 and are secured together with the interposed leg elastics 50 with a hot melt adhesive so that the leg elastics 50 may be contractibly secured under tension. Along respective inner portions of the leg elastic sheets 43 defined inboard of the leg elastics 50 as viewed in the transverse direction X and adapted to be secured to the base sheet 42, elongate reinforcing sheets 52 are interposed inside the respective doubled up leg sheets 51 and secured thereto with a hot melt adhesive so that the leg elastic sheets 43 may be stably secured to the base sheet 42.

As materials of the waist elastics 31, 32, 33, 34, for example, a thread, string or strand elastic material having a fineness in a range of 470 to 780 dtex and an elongation ratio in a range of 2.0 to 3.5 may be used. As materials of the leg elastics 50, a thread, string or strand elastic material having a fineness in a range of 310 to 620 dtex and an elongation ratio in a range of 2.0 to 3.0 may be used. In addition to the previously described elastic materials, as materials of the respective elastics, sheet-like elastic materials made of, for example, urethane having a predetermined width and thickness may be used.

The absorbent structure 11 has a longitudinally longer pad configuration and includes front and rear end portions 54, 55, an intermediate portion 56 and an absorbent core 58 extending at least across the crotch region, a body side liner 59 lying on the side of the skin-facing surface of the absorbent core 58 and a back sheet 60 lying on the side of the non-skin-facing surface of the absorbent core 58. Almost whole area of the non-skin-facing surface of the absorbent structure 11 is coated with a hot melt adhesive in a well known pattern. The front and rear end portions 54, 55 are secured to the skin-facing surfaces of the front and rear waist panels 18, 19 with a hot melt adhesive and the intermediate portion 56 is secured to the skin-facing surface of the crotch panel 13 with this hot melt adhesive. Referring to FIG. 3, the front end portion 54 of the absorbent structure 11 is secured to the skin-facing surface of the inner waist sheet 24 of the front waist panel 18, the rear end portion 55 lies between the inner waist sheet 25 and the outer waist sheet 27 of the rear waist panel 19 and secured to the skin-facing surface of the outer waist sheet 27. The front end portion 54 of the absorbent structure 11 is secured to the skin-facing surface of the inner waist sheet 24 and, in consequence, the elastic and relatively flexible inner waist sheet 24 comes in directly contact with the wearers skin. Thus the texture may be improved. The rear end portion 55 is secured between the inner waist sheet 25 and the outer waist sheet 27 and, in consequence, it will be possible to prevent bodily fluids from coming in direct contact with the wearers skin even if body exudate diffuse beyond the crotch region 16 to the portion of the absorbent structure 11 located in the rear waist region 15. The front and rear end portions 54, 55 of the absorbent structure 11 extend outwardly in the longitudinal direction Y beyond the front and rear ends of the leg elastic sheets 43 and a dimension in the longitudinal direction Y of the respective leg elastic sheets 43 is smaller than a dimension in the longitudinal direction Y of the absorbent structure 11.

The absorbent core 58 has a mass per unit area in a range of 400 to 600 $g/m^2$ and includes a mixture of fluff wood pulp and superabsorbent polymer particles (SAP), optionally added thermally synthetic staple fibers, and a liquid-permeable fibrous nonwoven fabric adapted to wrap the core material. As materials of the body side liner 59, various types of well known fibrous nonwoven fabrics having a mass per unit area in a range of about 10 to about 30 $g/m^2$ such as a spun bonded nonwoven fabric or an SMS nonwoven fabric may be used. As materials of the back sheet 60, for example, a liquid-impermeable spun bonded nonwoven fabric, an SMS nonwoven fabric, a plastic sheet of a laminate sheet of a fibrous nonwoven fabric and a breathable plastic sheet each having a mass per unit area in a range of about 10 to about 30 $g/m^2$ may be used. Though not illustrated, it is also possible to implement the present invention in a manner that the body side liner 59 and the back sheet 60 respectively have extension portions extending outwardly in the transverse direction X beyond the opposite lateral edges of the liquid-absorbent core 58 and a plurality of elastics of threads, strands or strings is contractibly attached under tension to these extension portions so that, during use of the diaper 10, three-dimensional barrier cuffs spacing away from the body side liner 59 and toward the wearer's crotch may be formed.

Figure 4:
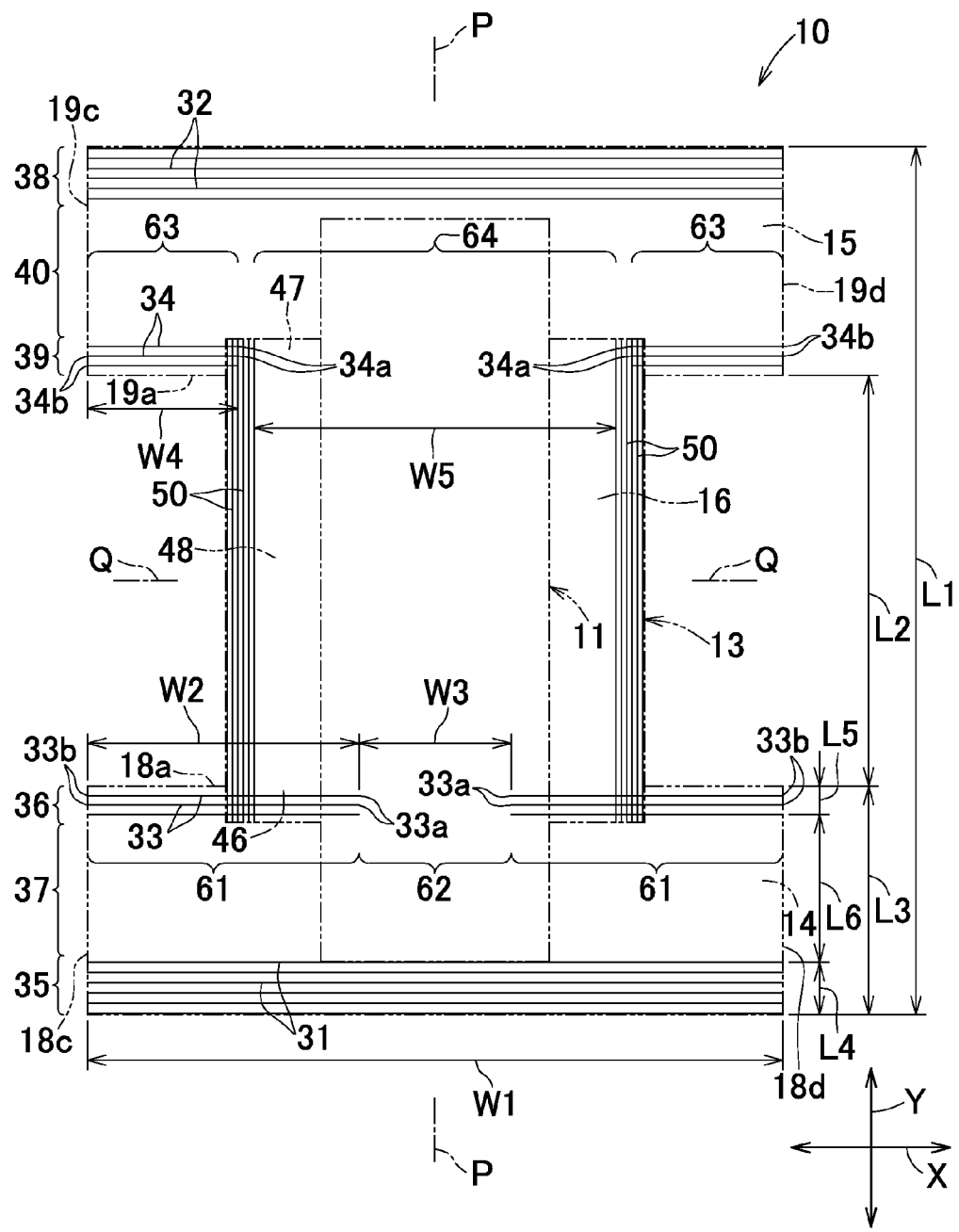
FIG. 4 is a developed plan view similar to FIG. 2 except that constituent elements other than the respective elastics are indicated by imaginary lines.

Referring to FIG. 4, a dimension L1 in the longitudinal direction Y of the diaper 10 is in a range of about 450 to about 550 mm, a dimension W1 in the transverse direction X of the diaper 10 is in a range of about 320 to about 380 mm and a dimension L2 in the longitudinal direction Y of the crotch region 16 is in a range of about 200 to about 280 mm. A dimension L3 in the longitudinal direction Y of the respective lateral edges 18d of the front waist region 14 is in a range of about 100 to about 140 mm, a dimension L4 in the longitudinal direction Y of the outer end portion 35 is in a range of about 15 to about 50 mm, a dimension L5 in the longitudinal direction Y of the inner end portion 36 is in a range of about 10 to about 30 mm and a dimension L6 in the longitudinal direction Y of the intermediate portion 37 is in a range of about 50 to about 90 mm. The above-mentioned dimensions of the front waist region 14 in the respective portions are substantially the same as those in the corresponding portions of the rear waist region 15.

In the inner end portion 36 of the front waist region 14, first side elastic zones 61 in which the first waist inner end elastics 33 are arranged and a first middle inelastic zone 62 extending in the transverse direction X between the first side elastic zones 61 in which none of the first waist inner end elastics 33 is arranged are defined. In the inner end portion 39 of the rear waist region 15, second side elastic zones 63 in which the second waist inner end elastics 34 are arranged and a second middle inelastic zones 64 extending in the transverse direction X between the second side elastic zones 63 in which none of the second waist inner end elastics 34 is arranged are defined. Regarding the dimensions of the respective zones, a dimension W2 in the transverse direction X of the respective first side elastic zones 61 is in a range of about 120 to about 140 mm, a dimension W3 in the transverse direction X of the first middle inelastic zone 62 is in a range of about 60 to about 100 mm, a dimension W4 in the transverse direction X of the respective second side elastic zones 63 is in a range of about 60 to about 90 mm and a dimension W5 in the transverse direction X of the second middle inelastic zone 64 is in a range of about 170 to about 210 mm The first middle inelastic zone 62 may be formed by a method as will be described (the second middle inelastic zone 64 also may be formed by the same method). For example, the zones of the outer waist sheet 26 to be formed with the first side elastic zones 61 are coated on the inner surface thereof with a hot melt adhesive in an appropriate pattern and the continuous first waist inner end elastics 33 are fed under tension onto the inner surface of the outer waist sheet 26 including these zones so that the first waist inner end elastics 33 may be secured to the adhesive-coated zones. At this state, the first waist inner end elastics 33 may be cut in the zone to be defined as the first middle inelastic zone 62 to ensure that the first waist inner end elastics 33 automatically contract (snap-back) since the segments of the first waist inner end elastics 33 are not secured to this zone 62 with the adhesive. As a result, the first waist inner end elastics 33 having a contractile force are substantially not present in the first middle inelastic zone 62. The terms "substantially not present" suggest that negligibly short segments of the first waist inner end elastics 33 may sometimes stay behind in the first middle inelastic zone 62 after the plurality of first waist inner end elastics 33 have been cut in the first middle inelastic zone 62. The first waist inner end elastics 33 are preferably cut in a single step so as to snap back without any segments remaining in the first middle inelastic zone. Alternatively, it is possible to cut off utterly the segments of the first waist inner end elastics 33 lying in the first middle inelastic zone 62 without relying on the snap back effect.

The method for defining the first and second middle inelastic zones 62, 64 is not limited to the method as has been described above and these inelastic zones 62, 64 may be defined with use of other methods. For example, the segments of the first waist inner end elastics 33 to be laid in the first middle inelastic zone 62 may be laid under no tension in the first middle inelastic zone 62. Here, the first inelastic region 62 may be coated with a hot melt adhesive and the first waist inner end elastics 33 may be secured under no tension. It is also possible to deprive or inhibit a contractile property of the first waist inner end elastics 33 laid under tension in the first middle inelastic zone 62, thereby making this zone inelastic. As has been described just above, the term "inelastic zones" used herein includes the case in which the first and second waist inner end elastics 33, 34 are substantially not present in the first and second middle inelastic zones 62, 64 and the case in which the first and second waist inner end elastics 33, 34 are present in these zones but these elastics develop no contractile property.

The first waist inner end elastics 33 respectively have outer end portions 33b lying on the opposite lateral edges 18c, 18d of the front waist region 14 and inner end portions 33a lying so as to overlap with the absorbent structure 11 wherein these first waist inner end elastics 33 are secured under tension between the inner and outer ends. The second waist inner end elastics 34 respectively have outer end portions 34b lying on the opposite lateral edges 19c, 19d of the rear waist region 15 and inner end portions 34a lying so as to overlap with the leg elastics 50 wherein the second waist inner end elastics 34 are secured under tension between the inner and outer ends. Such arrangement of the first and second waist inner end elastics 33, 34 ensures that the absorbent structure 11 may be kept in close contact with the wearers body in the inner end portion 36 of the front waist region 14 under the effect of contractile force of the first waist inner end elastics 33 and a gap inducing leakage of body exudate between the wearers body and the absorbent structure 11 should not be created even by movements of the wearer's thighs. In the inner end portion 39 of the rear waist region 15, the second waist inner end elastics 34 are free from intersecting with the absorbent structure 11 and, in consequence, the contractile force thereof should not be exerted on the absorbent structure 11 and develop crack and/or crease causing leakage of bodily fluids.

Figure 5:
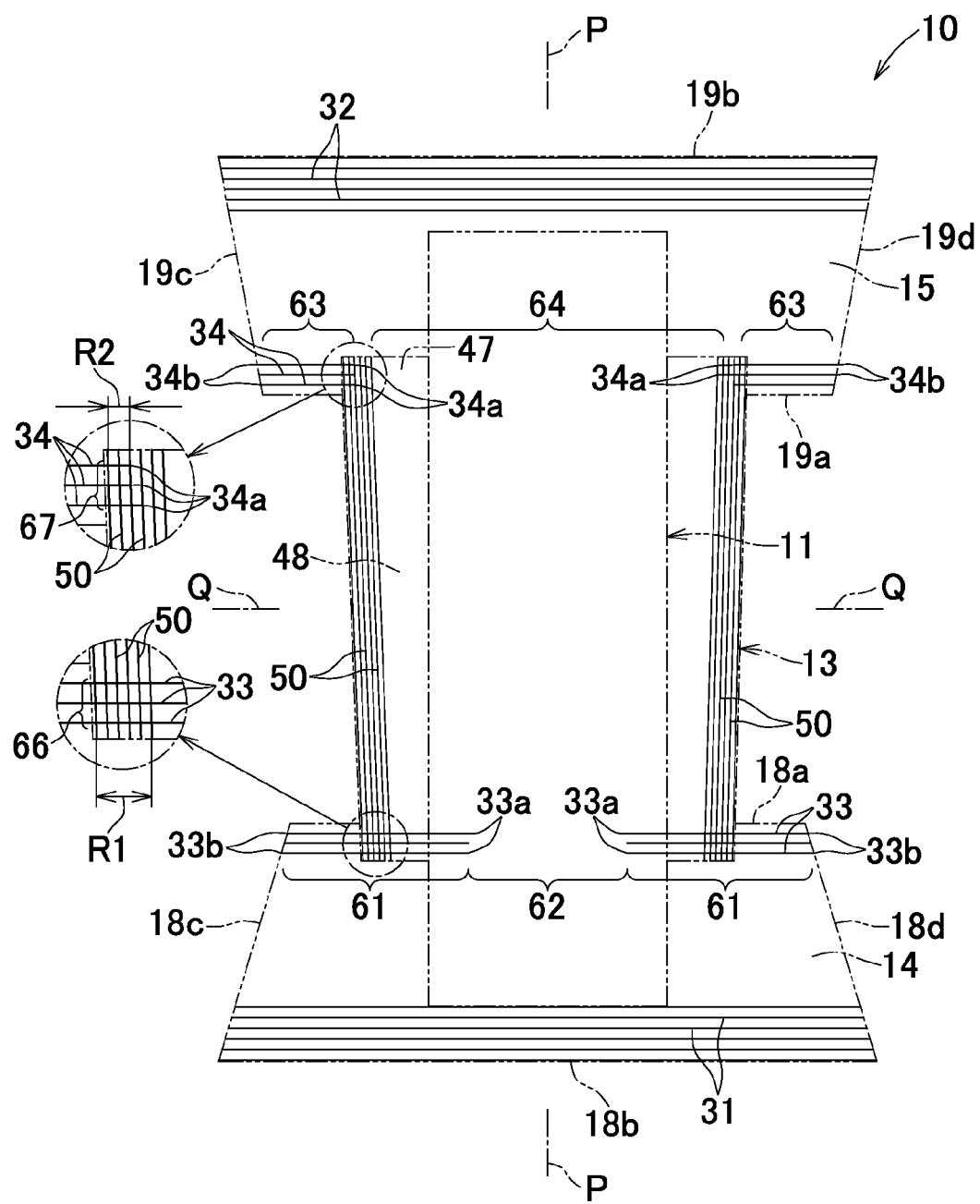
FIG. 5 is a developed plan view of the diaper flatly extended in the longitudinal direction and the transverse direction to predetermined elongation points of the respective elastics wherein the constituent elements other than the respective elastics are indicated by imaginary lines.

Referring to FIG. 5, it shows a developed plan view of the diaper 10 of which the front and rear waist regions 14, 15 are flatly extended in the longitudinal direction Y and the transverse direction X in the configuration of the diaper 10 would assume when placed on a wearer. In the front and rear waist regions 14, 15, the respective elastics are in a state of contraction and the dimensions in the transverse direction X of the front and rear waist regions 14, 15 are correspondingly smaller than those in FIG. 4. Specifically, in the front and rear waist regions 14, 15, the first and second side elastic zones 61, 63 contract and the first and second waist inner end elastics 33, 34 are pulled further inwardly under the contractile force of the leg elastics 50 intersecting with them, resulting in that the dimensions in the transverse direction X of the inner end edges 18a, 19a become smaller than those of the outer ends 18b, 19b. In consequence, the respective opposite lateral edges 18c, 18d; 19c, 19d gradually slope away from the outer ends 18b, 19b to the inner end edges 18a, 19a toward the longitudinal axis P-P.

In the inner end portion 39 of the rear waist region 15, the inner end portion 34a of the second waist inner end elastics 34 partially overlap with the leg elastics 50 and therefore only the segments of the second waist inner end elastics 34 located outboard of the leg elastics 50 in the transverse direction X contract without exerting any influence on the crotch panel 13 itself. In the inner end portion 36 of the front waist region 14, the respective inner end portions 33a of the first waist inner end elastics 33 are located inboard of the leg elastics 50 in the transverse direction X and therefore not only the segments of the first waist inner end elastics 33 located outboard of the leg elastics 50 in the transverse direction X but also the segments of the first waist inner end elastics 33 located inboard of the leg elastics 50 in the transverse direction X contract. Under the effect of such contraction of the first waist inner end elastics 33, the dimension in the transverse direction X of the front end portion 46 of the crotch panel 13 is reduced. Consequently, the leg elastics 50 gradually slope away inwardly from the rear side to the front side and the dimension in the transverse direction X of the crotch region 16 on the side of the front waist region 14 is smaller than the dimension in the transverse direction X of the crotch region 16 on the side of the rear waist region 15.

As used herein, the term "intersection" between the leg elastics 50 and the first waist inner end elastics 33 and/or the second waist inner end elastics 34 means that the reinforcing sheet 30 having the first and second waist inner end elastics 33, 34 secured thereon in a stretchable and contractible manner and the leg elastic sheet 43 having the leg elastics 50 secured thereon in a contractible manner are secured to each other so that the effectively extensible segments of the leg elastics 50 and the effectively extensible segments of the first waist inner end elastics 33 and/or the second waist inner end elastics 34 may substantially cooperate with each other.

Figure 6:
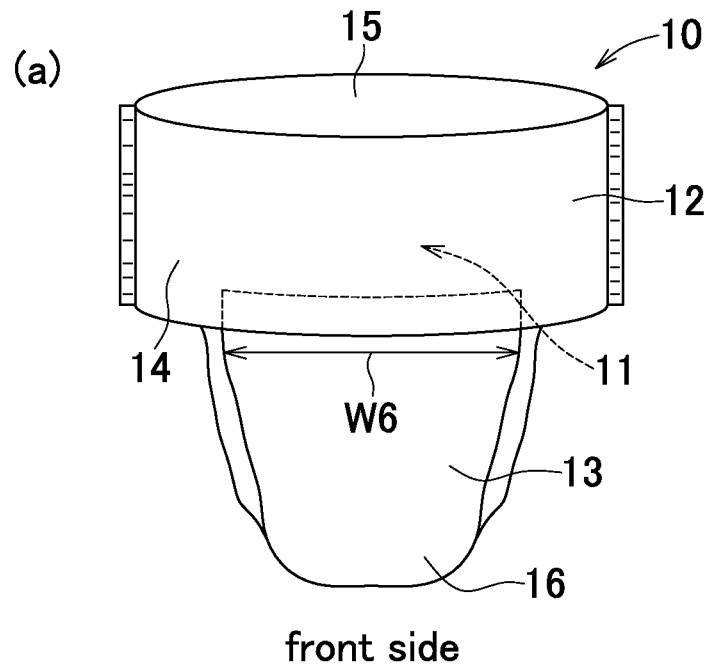
FIG. 6 (a) is a diagram of the diaper put on the wearer's body as viewed from the front and FIG. 6 (b) is a diagram of the diaper put on the wearer's body as viewed from a rear side.
Figure 6:
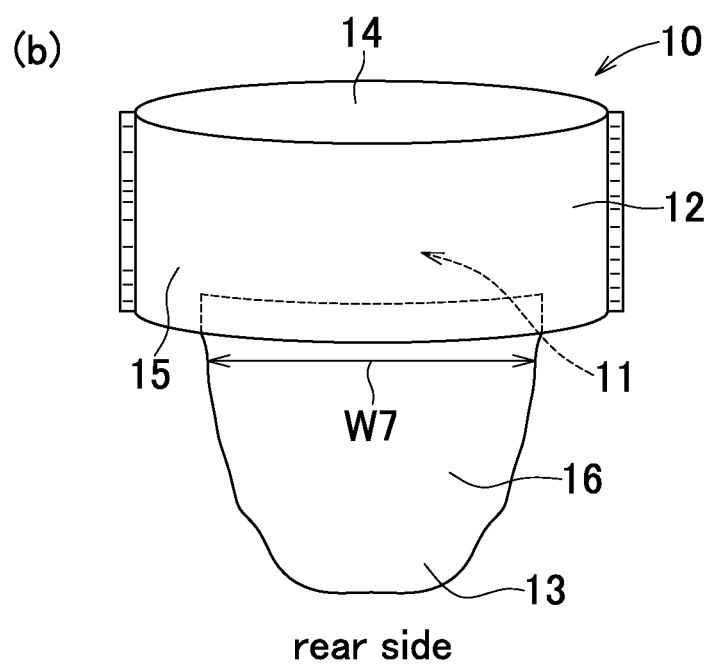

Referring now to FIG. 6 (a) and FIG. 6 (b), a dimension W6 in the transverse direction X of the portion extending along the inner end edge 18a of the crotch region 16 on the side of the front waist region 14 is smaller than a dimension W7 in the transverse direction X of the inner end edge 19a of the crotch region 19a on the side of the rear waist region 15 as has been described above. Specifically, the dimension W6 of the former is in a range of about 110 to about 130 mm and the dimension W7 of the latter is in a range of about 160 to about 180 mm. In this way, the dimension in the transverse direction X of the absorbent structure 11 is relatively small on the side of the front waist region 14 in the crotch region 16 and therefore the leg elastics 50 should not compress the wearer's groin and not encumber free movements of the wearer's thighs. On the side of the rear waist region 15 in the crotch region 16, the dimension in the transverse direction X of the absorbent structure 11 is relatively large and therefore the wearer's buttocks should not be exposed externally due to, for example, a situation that the leg elastics 50 are wedged in the wearer's posterior rugae.

To ensure the advantageous effect as has been described just above, a dimension R2 in the transverse direction X of respective second intersection zones 67 between the second waist inner end elastics 34 and the leg elastics 50 in the rear waist region 15 is preferably in a range of about 10 to about 30% of a total dimension R1 in the transverse direction X of the leg elastics 50 on the respective sides. If this ratio is lower than about 10% or if the second waist inner end elastics 34 do not intersect with the leg elastics 50 at all, it will be impossible to form a virtual elastic belt sufficiently pressed against the wearer's thighs to prevent leakage of bodily fluids and, in consequence, bodily fluids should not leak out of the diaper 10. If this ratio is higher than about 30%, the contractile force of the second waist inner end elastics 34 will interfere with the contractile property of the leg elastics 50 and, as a result, the opposite lateral portions of the absorbent structure 11 will contract so as to reduce the dimension W7 in the transverse direction X of the portion of the crotch region 16 on the side of the rear waist region 15 and, in consequence, the wearer's buttocks might be exposed externally.

Respective first intersection zones 66 in which the first waist inner end elastics 33 intersect with the leg elastic 50 in the front waist region have a dimension corresponding to the dimension R1 in the transverse direction X of the leg elastics 50 and the dimension R2 in the transverse direction X of the respective second intersections 67 is smaller than the dimension R1 in the transverse direction X of the respective first intersection zones 66.

Of the first and second side elastic zones 61, 63, at least the second side elastic zones 63 preferably have a tensile strength at a maximum elongation point higher than a tensile strength of at a maximum elongation point of the respective elastic zones defined by the leg elastics 50. As has previously been described, the intersection zones between the leg elastics 50 and the second waist inner end elastics 34 are relatively small, the leg elastics 50 are pulled outwardly in the transverse direction X under the effect of the tensile force of the second waist inner end elastics 34 to ensure that the absorbent structure 11 sufficiently cover the wearer's buttocks when the front and rear waist regions 14, 15 are pulled up to put on the diaper 10 so long as the tensile strength of the second side elastic zones 63 is higher than that of the elastic zones defined by the leg elastics 50. More specifically, the tensile strength of the second side elastic zones 63 at the maximum elongation point is in a range of about 3.0 to about 6.5 N/25 mm and the tensile strength of the elastic zones defined by the leg elastics 50 at the maximum elongation point is in a range of about 2.0 to about 2.9 N/25 mm wide. As used herein, the terms "tensile strength of the elastic zones at the maximum point" means the tensile strength thereof being measured as the diaper 10 flatly extended in the longitudinal direction Y and the transverse direction X to the extent that gathers/creases/wrinkles due to the contractile force of the elastics are visually disappeared.

Second Embodiment

Figure 7:
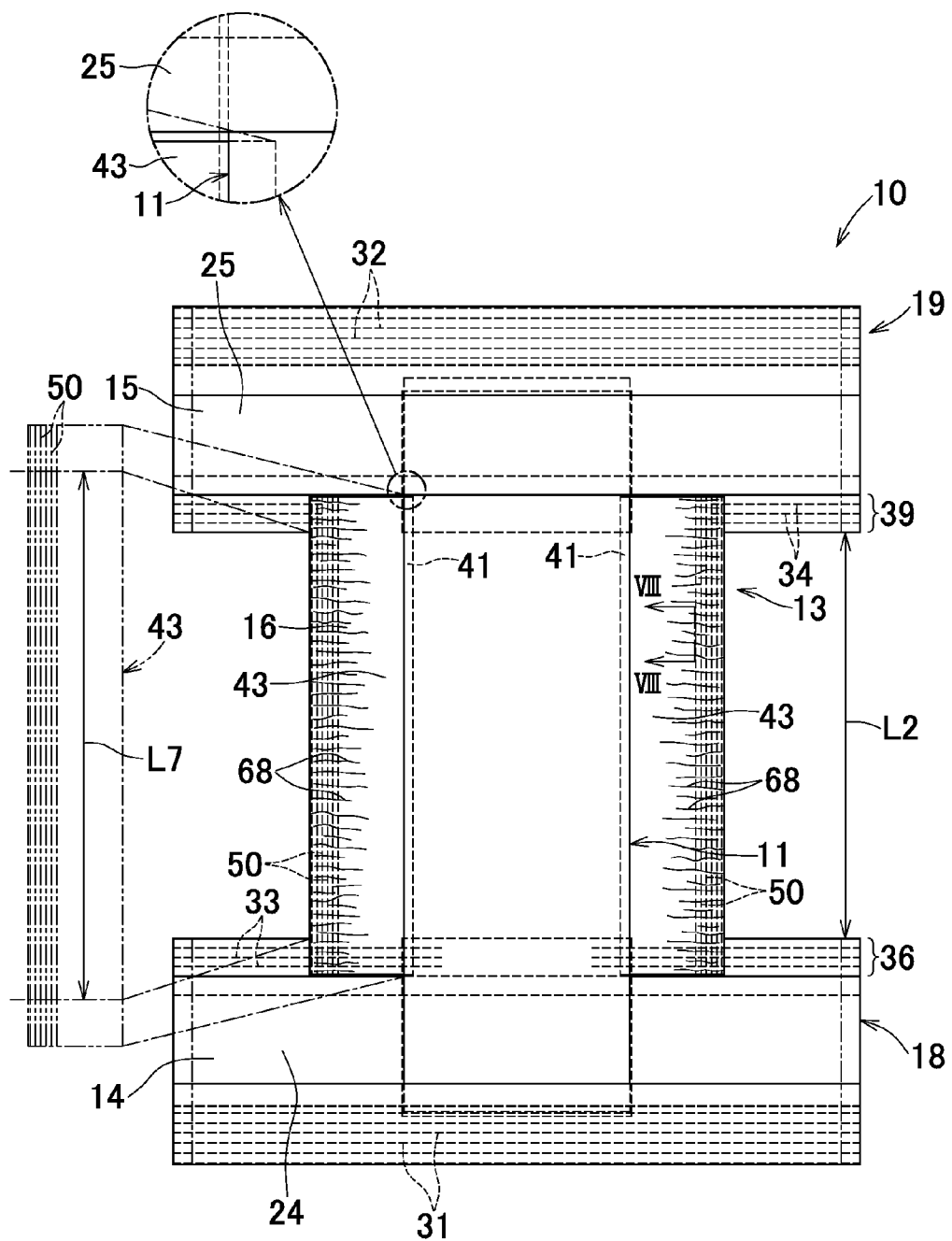
FIG. 7 is a developed plan view similar to FIG. 2, illustrating the diaper according to a second embodiment.

Referring to FIG. 7, it shows a developed plan view similar to FIG. 2, as the diaper 10 according to a second embodiment of the present invention. The basic construction of the diaper 10 according to this embodiment is similar to that of the first embodiment but distinguished from the first embodiment in aspects as will be described below.

Figure 8:
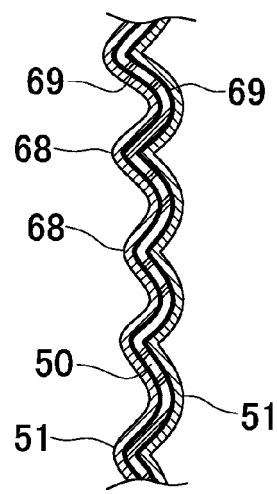
FIG. 8 is a sectional view taken along line VIII-VIII in FIG. 7.

According to this embodiment, the respective leg elastic sheets 43 constituting the crotch panel 13 are secured, in a contracted state, to the respective skin-facing surfaces of the base sheet 42 and the inner end portions 36, 39 of the front and rear waist regions 14, 15 so that the leg elastic sheets 43 may be formed with a plurality of gathers 68. Referring to FIG. 8, the leg elastics 50 are secured to the leg sheets 51 by the intermediary of joining zones 69 defined by a hot melt adhesive applied to whole circumference of the leg elastics 50 continuously in the longitudinal direction Y. In this regard, it is also possible to provide the joining zones 69 on the whole circumference of the leg elastics 50 at certain intervals in the longitudinal direction Y so long as these leg elastics 50 are attached to the leg sheets 51 in a contracted state.

The dimension in the longitudinal direction Y of the crotch region 16, i.e., the distance dimension L2 in the longitudinal direction Y between the inner end edge 18a of the front waist region 14 and the inner end edge 19a of the rear waist region 15 is in a range of 200 to 280 mm and an effectively extensible dimension L7 at the maximum elongation point of the respective leg elastic sheets 43 is in a range of about 230 to about 420 mm. The terms "effectively extensible dimension L4" used herein means a dimension in the longitudinal direction Y of the portion being stretchable in the longitudinal direction in the respective leg elastic sheets 43 extending between the inner end edge 18a of the front waist region 14 and the inner end edge 19a of the rear waist region 15 except the front and rear end portions 46, 47 which are secured to the front and rear waist regions 14, 15 and neither stretchable nor contractible. In this way, the respective leg elastic sheets 43 are elastically stretchable at a stretch ratio at least 1.05 or higher, preferably at a ratio in a range of 1.05 to 1.5 and more preferably at a ratio in a range of 1.1 to 1.4 to the dimension L2 in the longitudinal direction Y of the crotch region. In conventional diapers in which the front and rear waist regions and the crotch region are separately prepared and the leg elastics contractibly attached under tension, there has been a likelihood that a tensile strength required to act on the wearer's body might be insufficient and, as a result, the leg elastics 50 might be pulled inwardly, for example, due to movements of the wearer's thighs and wedged in the wearer's posterior rugae. In contrast, in the diaper 10 according to this embodiment, the leg elastic sheets 43 are attached in a contracted state so that the leg elastic sheets 43 are sufficiently stretched along the wearer's thighs to ensure the required tensile strength. In this way, the diaper 10 is stably kept in close contact with the wearer's thighs. In addition, the leg elastics 50 are pulled outwardly under the effect of contraction of the second side elastic zones 63 and therefore the dimension in the transverse direction X of the rear end portion 47 of the absorbent structure 11 is not changed or even enlarged in comparison to this dimension before the diaper 10 is put on the wearer's body. Thus, the wearer's buttocks should not be exposed externally.

A dimension ratio of the leg elastic sheets 43 included in the diaper 10 in the state of the product before and after the contraction may be calculated with use of a test piece composed of the leg elastic sheets 43 attached to the lateral edges of the base sheet 42 in the crotch region 16 being cut out together with the base sheet 42. More specifically, a test piece having an arbitrary length (e.g., 10 cm) in the longitudinal direction Y is cut out inclusively of the joint regions 41 from the base sheet 42 and the leg elastic sheets 43 in the region adjoining to the joint region 41 lying in the crotch region 16 of the diaper 10 so that the test pieces may have a rectangular configuration. Then, from the region adjoining to the joint region 41, the sheet member constituting the base sheet 42 and the leg elastic sheets 43 (i.e., the inner sheet 44, the outer sheet 45 and leg sheet 51) are cut into a predetermined width (e.g., 5 mm) and dimensions of the respective test pieces in the longitudinal direction Y are measured. For the reason that the leg elastic sheets 43 are attached in a contracted state to the lateral edges of the base sheet 42, the dimension of the sheet member (i.e., the leg sheet 51) constituting the leg elastic sheets 43 is larger than the dimension of the sheet member forming the base sheet 42. The dimensional ratio of the leg elastic sheets 43 before and after the contraction may be calculated from a dimensional ratio between the sheet member forming the leg elastic sheets 43 and the sheet member forming the base sheet 42.

Figure 9:
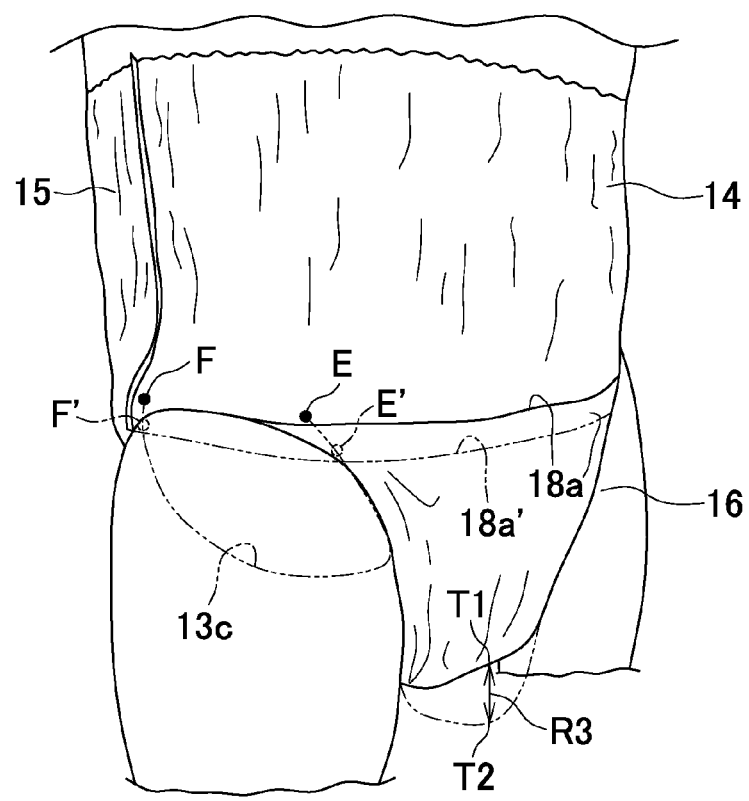
FIG. 9 is a perspective view of the diaper put on the wearer's body.

Referring to FIG. 9, assuming that a dimension L2 in the longitudinal direction Y of the crotch region 16 is smaller than a circumferential dimension of the wearer's thighs, the leg elastic sheets 43 will be stretched along the wearer's thighs so that the outer lateral edges 13c of the respective leg elastic sheets 43 may be located along the wearer's groins and the front end edge E and the rear end edge F may be located in vicinities of the wearer's ilium. In this situation, a bottom zone T1 of the crotch region 16 is kept in contact with the lowest zone of the wearer's crotch and ensures that body exudates are absorbed and contained by the absorbent structure. In contrast, assuming that the dimension L2 in the longitudinal direction Y of the crotch region 16 is smaller than the circumferential dimension of the wearer's thigh but the leg elastic sheets 43 are attached, in a state elongated to a dimension at the maximum elongation point thereof, to the front and rear waist regions 14, 15, the leg elastic sheets 43 will not be stretched any more from the situation in which the outer lateral edges 43c of the respective leg elastic sheets 43 are in contact with the wearer's groins. As a result, front and rear end edges E, F will be located at levels lower than the front and rear ends E, F. In such situation, a bottom zone T2 of the crotch region 16 will be located at a level lower than the bottom zone T1 and a differential dimension in the longitudinal direction Y of these bottom zones T1, T2 will be in a range of about 5 to about 10 mm. If the bottom zone T2 is located in a range of about 5 to about 10 mm lower than the wearer's crotch, the absorbent structure 11 might be spaced away from the wearer's crotch and might cause sideways leakage of body exudates. If the leg elastic sheets 43 already in the maximum elongation state are further pulled up in order to avoid such undesired situation, the peripheries of the respective leg-openings might be wedged in the wearer's posterior rugae with an appearance of a loincloth in back view. Thus, the diaper 10 might be disfigured.

Figure 10:
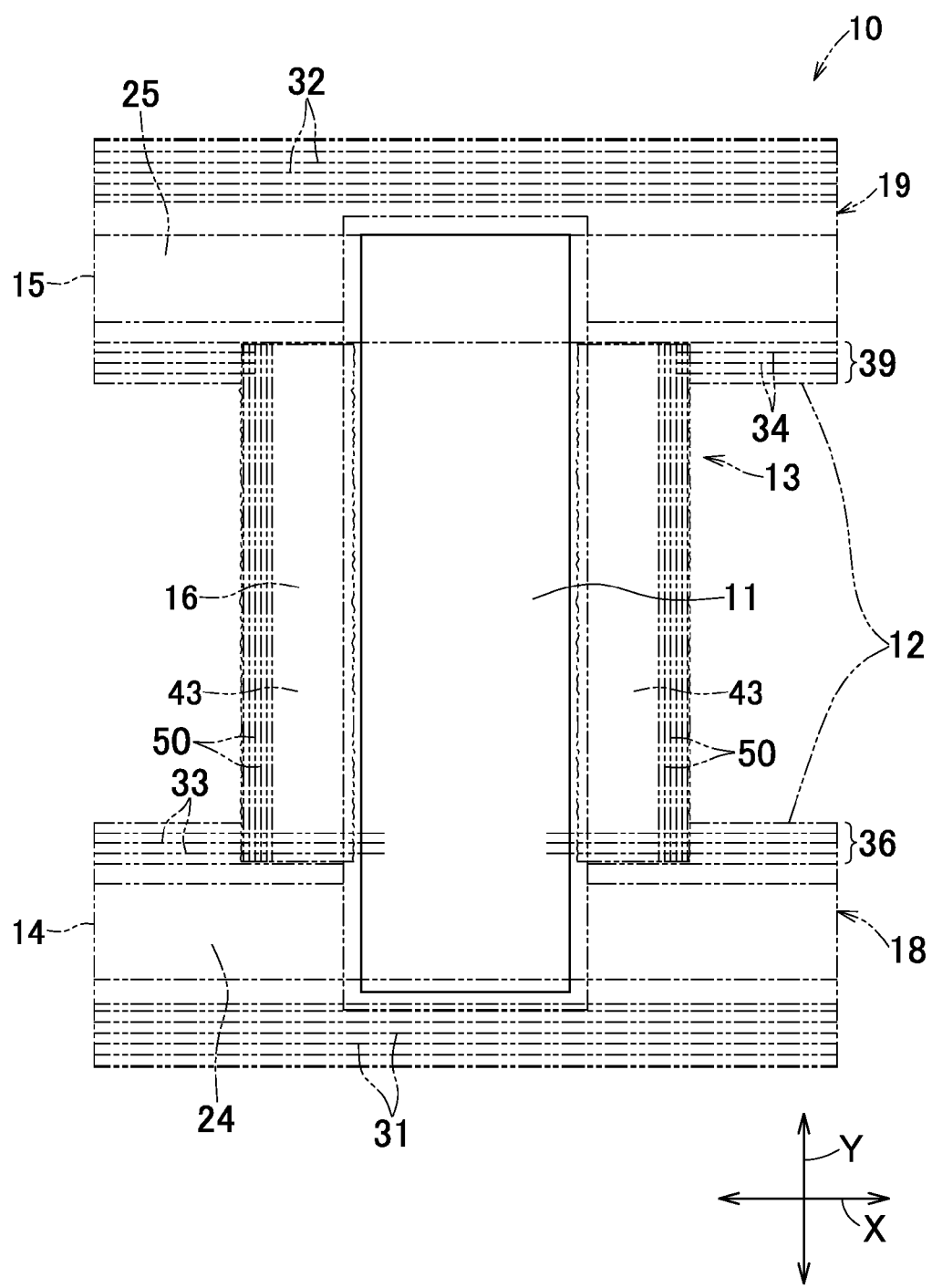
FIG. 10 is a developed plan view similar to FIG. 2, illustrating only the absorbent structure only by solid lines.

Referring to FIG. 10, the absorbent core 58 in the diaper 10 according to this embodiment has a rectangular configuration distinguished from the core often adopted by the conventional diapers such that the midsection of the core is concave inwardly and the width of the core is narrower than the width of the front and rear ends. Generally in pant-type diapers, when the wearer's legs are inserted through the leg-openings to put the diaper on the wearer's body, the opposite lateral edges of the absorbent core come in contact with the inner sides of the wearer's thighs and often interfere with pulling up the leg-openings' peripheries. In order that the leg-openings' peripheries may be pulled up to vicinities of the groins of the wearer, the opposite lateral edges of the absorbent core in the crotch region have been often formed to be concave inwardly to fit on the shapes of the thighs and the width of the midsection has been correspondingly narrowed. On the other hand, the crotch region is opposed to the excretory organ of the wearer and therefore the absorbent core must have a required absorption area. However, the lateral edges notched to concave inwardly have resulted in corresponding reduction of the effective area of the absorbent core 58 and deteriorated an absorption capacity. In contrast, as has previously been described, in the diaper 10 according to this embodiment, the leg elastic sheets 43 are further stretchable than the base sheet 42 in conformity with circumferential dimensions of the wearers thighs to ensure that the absorbent structure 11 is kept in close contact with the wearers body even when the opposite lateral edges of the absorbent structure 11 are not concavely curved. In this way, lack of the concave notches rather assures the absorbent structure 11 to have a desired area, thereby exerting a desired absorption performance. Specifically, a dimension in the transverse direction X (width dimension) of the midsection in the absorbent core 58 is in a range of 90% to 110% of a width dimension of the front and rear end portions located in the front and rear waist regions 14, 15, respectively. In other words, the midsection has substantially the same width dimension as that of the front and rear end portions even when the midsection is slightly concave or convex.

The absorbent structure 11 has an area in a range of about 450 to 630 $cm^2$ (in infant diapers of M-size-XXL-size) and the crotch region 16 has an area in a range of about 495 to 595 cm² (in infant diapers of M-size-extra L-size). Namely, the crotch region 16 has an area corresponding to about 94 to about 110% of that of the absorbent structure 11. Generally in pull-on type diapers, when the crotch region 16 is configured to have a relatively large area, respective areas of the leg-openings are likely to be restricted and, in consequence, smooth insertion of the wearer's legs therethrough becomes difficult. To solve this problem, according to this embodiment, the leg elastic sheets 43 are attached in a relaxed state to the crotch panel 13 so that the regions (elastic regions) provided with the leg elastics 50 may assume a planar posture extending outwardly (or hang down) and widely extend outwardly. In this way, the leg-openings should be easy to put the wearer's legs therethrough.

Third Embodiment

Figure 11:
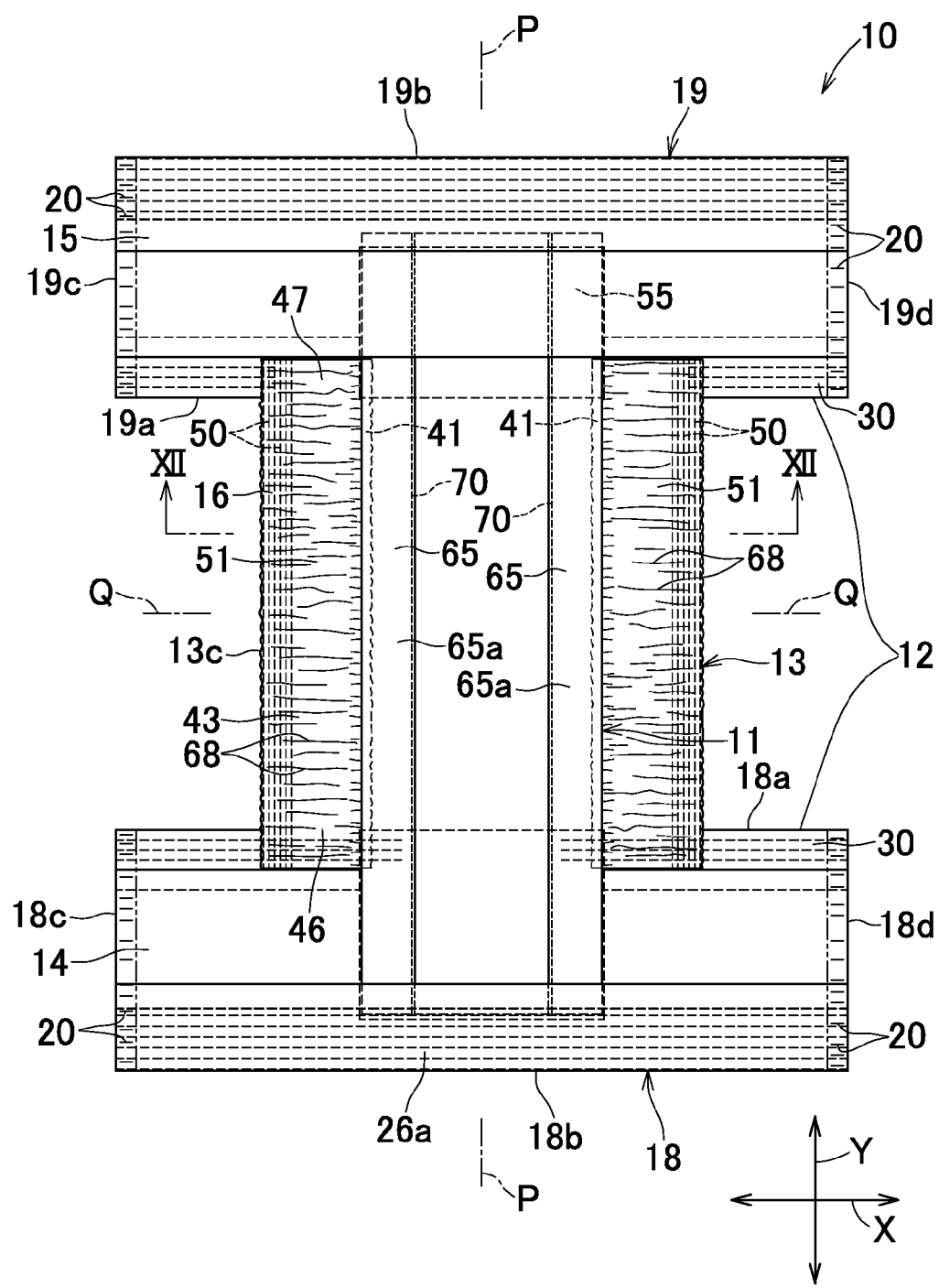
FIG. 11 is a developed plan view of the diaper according to third embodiment.
Figure 12:
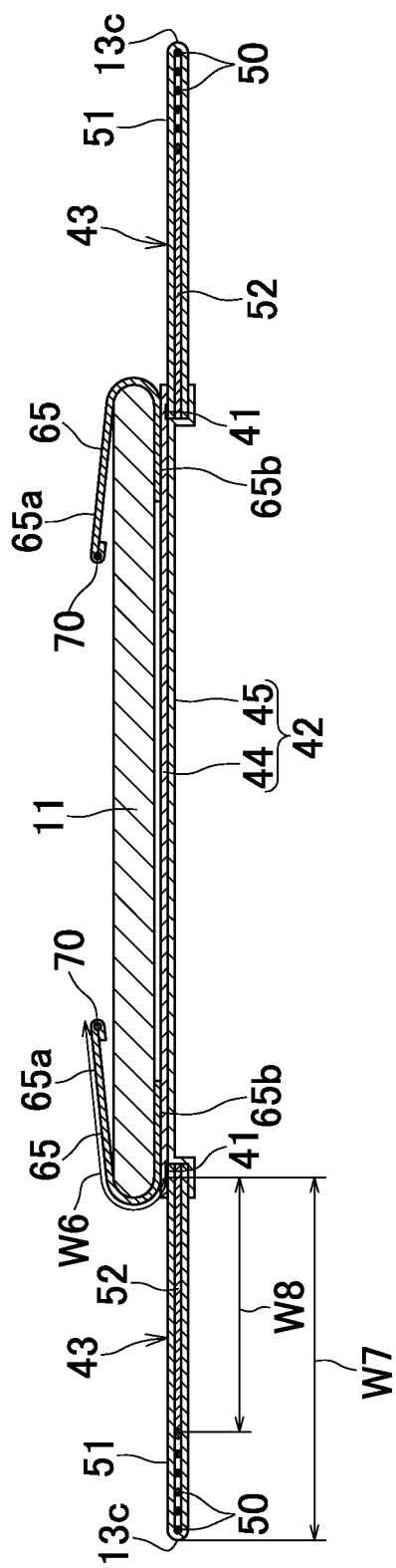
FIG. 12 is a schematic sectional view taken along line XII-XII in FIG. 11.
Figure 13:
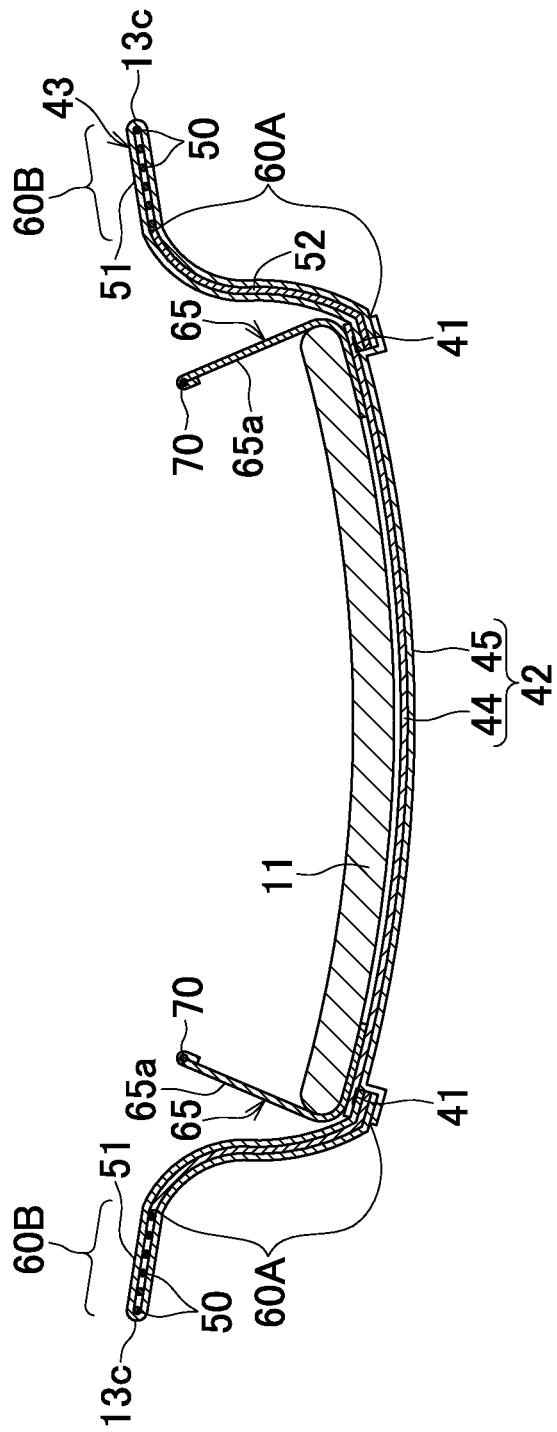
FIG. 13 is a schematic sectional view similar to FIG. 11, illustrating the diaper put on the wearer's body.

Referring to FIGS. 11 through 13, according to this embodiment also, the leg elastic sheets 43 are attached in a contracted (relaxed) state to the skin-facing surfaces of the base sheet 42 and the inner end portions 36, 39 of the front and rear waist regions 14, 15, respectively, in the same manner as in the second embodiment and, in consequence, the leg elastic sheets 43 are formed with a plurality of gathers 68 even when the front and rear waist regions 14, 15 and the absorbent structure 11 are developed until the gathers disappear therefrom. According to this embodiment, the absorbent structure 11 is provided on its outer surface with a pair of barrier sheets 65. Each of the barrier sheets 65 has one lateral portion attached to the inner surface (the surface opposed to the base sheet 42) of the absorbent structure 11 and has front and rear fixed end portions secured to the skin-facing surface of the elastic waist panel 12 in the front and rear waist regions 14, 15, a proximal edge portion 65*b* extending in the longitudinal direction Y between the front and rear fixed end portions and a free distal edge portion 65*a* opposed to the proximal edge portion 65*b* in the transverse direction X and defined by the inner edge portion of the barrier sheet 65 folded inwardly. Each of the distal edge portions 65*a* is provided with thread, strand or string cuff elastics 70 contractibly attached thereto. In the diaper 10 put on the wearer's body, the distal edge portions 65*a* are spaced away from the skin-facing surface of the liquid absorbent structure 11 under contraction of the cuff elastics 70 and define a pair of barrier cuffs serving to prevent body exudates from leaking sideways. In this regard, the barrier cuffs are not limited to inwardly-collapsed type barrier cuffs used in this embodiment but it is also possible to use outwardly-collapsed type barrier cuffs or the barrier cuffs having the front and rear end portions secured in an inwardly-collapsed state and having the distal lateral edges collapsed outward.

In the conventional pant-type disposable diapers, as has previously described, the absorbent structure and the wearer's body are apt to be spaced away from each other in a state that the leg-openings' peripheries are in close contact and, in consequence, body exudates are likely to leak sideways. To prevent leakage of body exudates, the barrier cuffs are configured to have a relatively large height dimension. However, the larger the height dimension of the barrier cuffs is, the more the number of the cuff elastics needs to be increased and, as a result, these barrier cuffs stand up under the effect of these increased number of the cuff elastics and the leg-openings are apt to be closed thereby. Thus, it may not be easy to smoothly put the wearer's legs through the respective leg-openings. In contrast to the conventional pant-type disposable diaper, in the diaper 10 according to this embodiment, the absorbent structure 11 and the wearer's body may be kept in close contact with each other in a state that the leg elastic sheets 43 defining the leg-openings' peripheries are put in close contact with the wearer's thighs. Consequently, the height dimension W6 of the barrier cuffs (corresponding to the dimension in the transverse direction X of the respective barrier cuffs in the diaper 10 in its developed state, in other words, corresponding to the distance dimension W6 from the fixed lateral portions located on the rear surface of the absorbent structure 11 to the top portions provided with the cuff elastics 70) may be set to be relatively small so that the wearer's legs may unlikely be caught by the barrier cuffs and may be put smoothly through the leg-openings. In addition, the leakage barrier cuffs adapted to rise and contact with the wearer's body are provided in the crotch region 16, whereby the leakage barrier cuffs cooperate with the gasket cuffs defined by the leg elastic sheets 43 extending outwardly along the wearer's thighs to form effective double barriers against leakage of body exudates.

More specifically, a height dimension W6 of the barrier cuff is in a range of about 15 to about 40 mm, preferably in a range of 20 to 35 mm During use of the diaper 10, inelastic regions 60A lying between the respective lateral edges of the absorbent structure 11 to the respective groups of the leg elastics 50 in the leg elastic sheets rise like barriers to form the gasket cuffs, and elastic regions 60B provided with the leg elastics 50 extend outwardly along the wearer's thighs. The height dimension W6 of the barrier cuff is preferably smaller than a dimension W7 in the transverse direction X from the lateral edges of the absorbent structure 11 in the leg elastic sheets 43 to the outer edges 13*c*, more preferably smaller than a dimension W8 (a height dimension of the gasket cuff in a state that the inelastic regions 62A are rising, more specifically, a distance dimension from the joint region 41 to a portion where an innermost elastic of the leg elastics 50 is located) in the transverse direction X of the respective inelastic regions 62A. These height dimensions W6, W7 and W8 may be adjusted in this manner not only to prevent the wearer's legs from being caught by the barrier cuffs but also to allow the leg-openings' peripheries to stably fit the wearer's thighs and, further, the gasket cuffs defined by the inelastic regions 60A having a further larger height may block movements of body exudates. While the wearer's toes may sometimes come in contact with the inelastic regions 60A (gasket cuffs) having the height dimension larger than that of the barrier cuffs, the wearer's toes may be further put through the leg-openings so as to collapse the inelastic regions 60A since the leg elastic sheet 43 are attached in a state being overfed and the gasket cuffs are adapted to rise moderately and the elastic regions 60B extend outwardly continuously from the tops of the respective gasket cuffs along the wearer's thighs. In this way, the wearer's toes should not be caught by the inelastic regions 60A and break part of the inelastic regions 60A.

<Process of Manufacturing the Crotch Panel 13>

Figure 14:
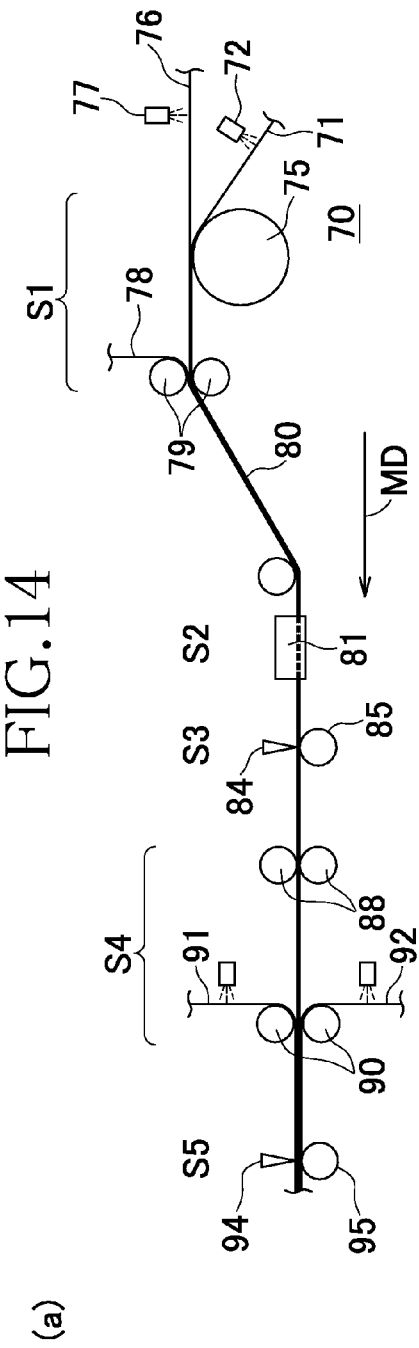
FIG. 14 (a) is a schematic diagram illustrating an apparatus of manufacturing the crotch panel and FIG. 14 (b) is a diagram illustrating appearance of continuous composite sheet in the process of manufacturing the crotch panel.
Figure 14:
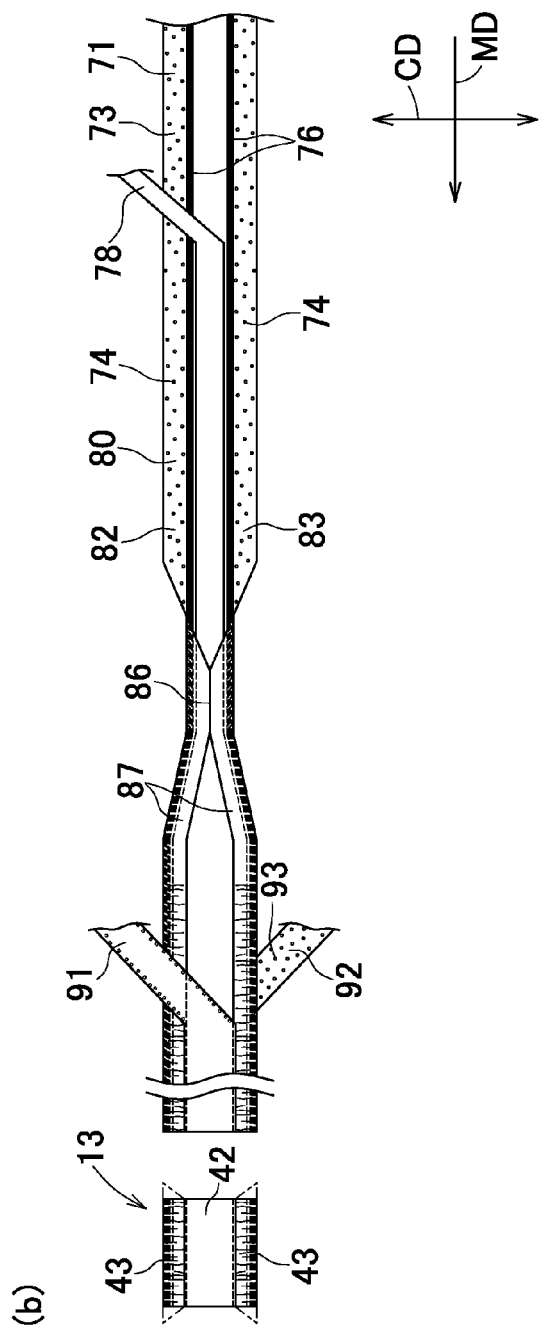

Referring to FIG. 14 (*a*), an apparatus 70 for manufacturing the crotch panel 13 exemplified herein includes a step S1 of attaching the continuous elastics, a step S2 of folding, a step S3 of cutting, a snap-back attachment step S4 and a second cutting step S5 in this order in the machine direction MD. FIG. 14 (*b*) illustrates states of the continuous composite sheet in the respective steps S1 through S5.

<Continuous elastics attachment step S1>

A continuous sheet 71 as base material for the previously described leg sheets 51 is fed from a feed roller (not shown) and coated by a coater 72 on a first surface 73 along lateral portions opposite to each other in the cross direction CD with a hot melt adhesive. Then the continuous sheet 71 is fed to a rotary drum 75 and a pair of continuous elastics 76 as base material for the leg elastics 50 is fed onto the first surface 73 of the continuous sheet 71 on the rotary drum 75. The continuous elastics 76 have previously been coated by a coater 77 on whole circumference thereof and in the machine direction MD with a hot melt adhesive and secured to the first surface 73 of the continuous sheet 71 with the hot melt adhesive. Then, the continuous sheet 71 and continuous plastic film 78 as base material for the reinforcing sheet 52 are fed and pressed between a pair of press rollers 79 so as to locate the continuous plastic film 78 between the pair of the continuous elastics 76 on the first surface 73. The surface of the continuous plastic film facing the first surface 73 of the continuous sheet 71 has previously been coated with a hot melt adhesive and the continuous plastic film 78 is secured to the continuous sheet 71 with the adhesive to form continuous composite sheet 80.

<Folding Step S2>

Lateral portions 82, 83 opposite to each other in the cross direction CD of the continuous composite sheet 80 are folded inwardly by a sailor (folding device) 81 and the inner surface of each of the folded lateral portions 82, 83 is bonded to itself with a hot melt adhesive together with the continuous elastics interposed between the folded inner surfaces.

<First Cutting Step S3>

The continuous composite sheet 80 is fed into a gap between a cutter 84 and an anvil roller 85 located so as to face each other and a midsection 86 in the cross direction CD thereof is cut so as to bisect the continuous composite sheet 80 and to form separated regions 87.

<Snap-Back Attachment Step S4>

The continuous composite sheet 80 is fed between a pair of circumferential velocity regulating rollers 88. Then, continuous sheets 91, 92 as base materials for the inner waist sheet 44 and the outer waist sheet 45, respectively, are fed by a pair of feed rollers 90 to the first surface 73 and the surface opposite thereto of the continuous composite sheet 80. The continuous sheets 91, 92 have previously been coated along the opposite lateral edges with a hot melt adhesive 93 with which the separated regions 87 are secured. A circumferential velocity V1 of the circumferential velocity regulating rollers 88 is higher than a circumferential velocity V2 of the feed rollers 90 and a ratio of the circumferential velocity V1 to the circumferential velocity V2 (i.e., V1/V2×100) is in a range of about 105 to about 150%, preferably in a range of about 110 to about 140%. In other words, the circumferential velocity regulating rollers 88 rotate at a circumferential velocity in a range of 1.05 to 1.5 times, preferably in a range of 1.1 to 1.4 times of the circumferential velocity V2 of the feed rollers 90. In this way, the separated regions 87 contract between the circumferential velocity regulating rollers 88 and the feed rollers 90 and consequentially the feed rollers 90 are fed with a quantity per unit time (second) of the continuous composite sheet 80 larger than a quantity per unit time (second) thereof fed in the other steps S1 to S3 and the separated regions 87 are attached in a contracted state to the continuous sheets 91, 92.

<Second Cutting Step S5>

The continuous composite sheet 80 is fed between a gap defined between a cutter 94 and an anvil 95 opposite to each other and cut along a cut line extending in the cross direction CD to form a plurality of crotch panels 13. As indicated by imaginary lines, while the portions of the individual crotch panel 13 provided with the leg elastics 50 of the leg elastic sheet 43 would otherwise be in an elongated state, these portions may be contracted under the effect of the circumferential velocity regulating rollers 88 to the dimension corresponding to the length dimension L2 in the longitudinal direction Y of the crotch region 13 before the crotch panel 13 is attached to the elastic waist panel 12.

The method for attaching the leg elastic sheet 43 in a contracted state to the base sheet 42 is not limited to the above-mentioned method. For example, it is possible to replace the circumferential velocity regulating rollers by gear rollers adapted for mechanically shaping the leg elastic sheet 43 to be undulating and to attach the leg elastic sheet 43 in such an undulating state to the base sheet 42.

The constituent elements of the disposable diaper 10 are not limited to those described in the specification but the other types of material widely used in the relevant technical field may be used without limitation unless otherwise stated. The terms "first", "second", "third" and "fourth" used in the description and claims of the present invention are used merely to distinguish the similar elements, similar positions or other similar means.

The disclosure described above may be arranged in at least the following features.

A disposable wearing article having a longitudinal direction and a transverse direction being orthogonal to the longitudinal direction, including:

a skin-facing surface;

a non-skin-facing surface;

a front waist region;

a rear waist region;

a crotch region extending between the front and rear waist regions;

an annular elastic waist panel defining the front and rear waist regions;

a crotch panel defining the crotch region; and an absorbent structure joined to the elastic waist panel, wherein:

the front waist region includes outer and inner end edges spaced apart from and opposite to each other in the longitudinal direction, a pair of first side elastic zones extending in the transverse direction and spaced apart from and opposite to each other in the transverse direction, and a first middle inelastic zone lying between the first side elastic zones;

the rear waist region includes outer and inner end edges spaced apart from and opposite to each other in the longitudinal direction, a pair of second side elastic zones extending in the transverse direction and spaced apart from and opposite to each other in the transverse direction and a second middle inelastic zone lying between the first side elastic zones;

the crotch panel includes a front end portion secured to the front waist region, a rear end portion secured to the rear waist region, and a pair of leg elastics extending in the longitudinal direction and intersecting with the first and second side elastic zones;

a dimension in the transverse direction of the second middle inelastic zone is larger than a dimension in the transverse direction of the first middle inelastic zone; and a dimension in the transverse direction of a first intersection zone in which the first side elastic zone and the leg elastics intersect with each other is larger than a dimension in the transverse direction of a second intersection zone in which the second side elastic zone and leg elastics intersect with each other.

The feature disclosed above may include at least the following embodiments.

(1) The absorbent structure lies in a midsection in the transverse direction of the crotch panel, the first side elastic zones extend from opposite lateral edges of the front waist region to the absorbent structure and the second side elastic zones extend from opposite lateral edges of the rear waist region to the leg elastics.

(2) Of the first and second side elastic zones, at least the second side elastic zone has a tensile strength at a maximum elongation point is higher than a tensile strength at a maximum elongation point of the elastic zone defined by the leg elastics.

(3) A dimension in the transverse direction of the second intersection zone lying in the rear waist region is in a range of about 10 to about 30% of a dimension in the transverse direction of the leg elastics.

(4) A dimension in the longitudinal direction of the front waist region is substantially the same as a dimension in the longitudinal direction of the rear waist region and inner end edges of the front and rear waist regions rectilinearly extending in the transverse direction are substantially orthogonal to the leg elastics.

(5) The crotch panel includes a base sheet and a pair of leg elastic sheets including the leg elastics and attached to opposite lateral portions of the base sheet.

(6) A dimension of the respective leg elastic sheets in the longitudinal direction is smaller than a dimension in the longitudinal direction of the absorbent structure.

(7) The leg elastic sheets are attached to the base sheet of the crotch panel so as to be formed with gathers extending in the transverse direction and an effective elongation dimension of the leg elastic sheet at the maximum elongation point is larger than a distance dimension in the longitudinal direction from the inner end edge of the front waist region to the inner end edge of the rear waist region.

(8) The effective elongation dimension of the leg elastic sheet at the maximum elongation point is in a range of about 1.05 to about 1.5 times of the distance dimension in the longitudinal direction from the inner end edge of the front waist region to the inner end edge of the rear waist region.

(9) The absorbent structure includes an absorbent core having a substantially rectangular configuration of which opposite lateral edges rectilinearly extend in the longitudinal direction.

(10) An area of the crotch region is in a range of about 94 to about 110% of the area of the absorbent structure.

(11) The absorbent structure is provided on opposite lateral portions thereof with a pair of liquid-impermeable barrier sheets each including front and rear fixed portions, a proximal edge portion defined between the front and rear fixed portions, and a distal edge portion extending inwardly in the transverse direction from the proximal edge portion, the respective distal edge portions of the barrier sheets are provided with cuff elastics attached thereto in a state being elastically stretchable and contractible, and a dimension in the transverse direction of the respective barrier cuffs in a rising state under contraction of the cuff elastics of the barrier sheets is smaller than a dimension in the transverse direction from the lateral edges of the absorbent structure to the outer lateral edges of the leg elastic sheets.

REFERENCE SIGNS LIST 10 disposable wearing article (disposable diaper)
11 absorbent structure
12 elasticized waist panel
13 crotch panel
14 front waist region
15 rear waist region
16 crotch region
18a inner end edge of front waist region (inner end edge of front waist panel)
18b outer end edge of front waist region (outer end of front waist panel)
18c, 18d lateral edges of the front waist region
19a lower end edge of rear waist region (inner end edge of rear waist region)
19b upper end edge of rear waist region (outer end edge of rear waist region)
19c, 19d lateral edges of rear waist region
42 base sheet
43 leg elastic sheet
50 leg elastics
61 first side elastic zone
62 first middle inelastic zone
63 second side elastic zone
64 second middle inelastic zone
65 barrier sheets
66 first intersection zone
67 second intersection zone
W6 dimension in transverse direction of barrier cuff
W7 dimension in transverse direction of inelastic region (gasket cuff)
L7 length dimension of leg elastic sheet at maximum elongation
R1 dimension in transverse direction of first intersection zone
R2 dimension in transverse direction of second intersection zone (dimension in transverse direction of leg elastics)
W2 dimension in transverse direction of first side elastic zone
W3 dimension in transverse direction of first middle inelastic zone
W4 dimension in transverse direction of second side elastic zone
W5 dimension in transverse direction of second middle inelastic zone
W6 dimension in transverse direction of barrier cuff
W7 dimension in transverse direction from lateral edges of absorbent structure to outer side edge in leg elastic sheet
X transverse direction
Y longitudinal direction

The invention claimed is:

1. A disposable wearing article having a longitudinal direction and a transverse direction being orthogonal to the longitudinal direction, said wearing article comprising:
a skin-facing surface;
a non-skin-facing surface;
a front waist region;
a rear waist region;
a crotch region extending between the front and rear waist regions;
an annular elastic waist panel defining the front and rear waist regions;
a crotch panel defining the crotch region; and
an absorbent structure joined to the elastic waist panel,
wherein:
the front waist region includes
outer and inner end edges spaced apart from and opposite to each other in the longitudinal direction,
a pair of first side elastic zones extending in the transverse direction and spaced apart from and opposite to each other in the transverse direction, and
a first middle inelastic zone lying between the first side elastic zones;
the rear waist region includes
outer and inner end edges spaced apart from and opposite to each other in the longitudinal direction,
a pair of second side elastic zones extending in the transverse direction and spaced apart from and opposite to each other in the transverse direction, and a second middle inelastic zone lying between the second side elastic zones;

the crotch panel includes
- a front end portion secured to the front waist region,
- a rear end portion secured to the rear waist region,
- a base sheet, and
- attached to opposite lateral portions of the base sheet, each leg elastic sheet including leg elastics extending in the longitudinal direction and intersecting with the first and second side elastic zones;

a dimension in the transverse direction of the second middle inelastic zone is larger than a dimension in the transverse direction of the first middle inelastic zone, a dimension in the transverse direction of first intersection zones in which the respective first side elastic zones and the respective leg elastics intersect with each other is larger than a dimension in the transverse direction of second intersection zones in which the respective second side elastic zones and the respective leg elastics intersect with each other, the leg elastic sheets are attached to the base sheet of the crotch panel so as to be formed with gathers extending in the transverse direction, an effective elongation dimension of the leg elastic sheets at a maximum elongation point is larger than a distance dimension in the longitudinal direction from the inner end edge of the front waist region to the inner end edge of the rear waist region, the absorbent structure is provided on opposite lateral portions thereof with a pair of liquid-impermeable barrier sheets each including
- front and rear fixed portions,
- a proximal edge portion defined between the front and rear fixed portions, and
- a distal edge portion extending inwardly in the transverse direction from the proximal edge portion, the respective distal edge portions of the barrier sheets being provided with a respective cuff elastic attached thereto in a state being elastically stretchable and contractible, and a dimension in the transverse direction of the respective barrier sheets in a rising state under contraction of the cuff elastics is smaller than a dimension in the transverse direction from lateral edges of the absorbent structure to outer lateral edges of the leg elastic sheets.

2. The wearing article according to claim 1, wherein
the absorbent structure lies in a midsection in the transverse direction of the crotch panel,
the first side elastic zones extend from opposite lateral edges of the front waist region to the absorbent structure, and
the second side elastic zones extend from opposite lateral edges of the rear waist region to the leg elastics.

3. The wearing article according to claim 1, wherein, of the first and second side elastic zones, at least the second side elastic zone has a tensile strength at a maximum elongation point higher than a tensile strength at a maximum elongation point of respective elastic zones defined by the respective leg elastics.

4. The wearing article according to claim 1, wherein a dimension of respective second intersection zones lying in the rear waist region in the transverse direction is in a range of about 10 to about 30% of a dimension of the respective leg elastics in the transverse direction.

5. The wearing article according to claim 1, wherein
a dimension of the front waist region in the longitudinal direction is substantially the same as a dimension of the rear waist region in the longitudinal direction, and
the inner end edges of the front and rear waist regions rectilinearly extending in the transverse direction are substantially orthogonal to the leg elastics.

6. The wearing article according to claim 3, wherein a dimension of the leg elastic sheets in the longitudinal direction is smaller than a dimension of the absorbent structure in the longitudinal direction.

7. The wearing article according to claim 1, wherein the effective elongation dimension of the respective leg elastic sheets at the maximum elongation point is in a range of about 1.05 to about 1.5 times the distance dimension in the longitudinal direction from the inner end edge of the front waist region to the inner end edge of the rear waist region.

8. The wearing article according to claim 1, wherein the absorbent structure includes an absorbent core and the absorbent core has a substantially rectangular configuration of which opposite lateral edges rectilinearly extend in the longitudinal direction.

9. The wearing article according to claim 1, wherein an area of the crotch region is in a range of about 94 to about 110% of the area of the absorbent structure.

\* \* \* \* \*